US006703517B2

United States Patent
Hattori et al.

(10) Patent No.: US 6,703,517 B2
(45) Date of Patent: Mar. 9, 2004

(54) METHOD FOR PREPARING N-LONG CHAIN ACYL NEUTRAL AMINO ACID

(75) Inventors: Tatsuya Hattori, Kawasaki (JP); Nobuyoshi Kitamura, Kawasaki (JP); Naoya Yamato, Kawasaki (JP); Hirofumi Yokota, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/301,616

(22) Filed: Nov. 22, 2002

(65) Prior Publication Data

US 2003/0125227 A1 Jul. 3, 2003

(30) Foreign Application Priority Data

Nov. 26, 2001 (JP) ........................... 2001-359117

(51) Int. Cl.$^7$ ............................................. C07C 231/00
(52) U.S. Cl. ........................... 554/69; 554/68; 510/119; 510/126
(58) Field of Search .................... 584/68, 69; 510/119, 510/124

(56) References Cited

U.S. PATENT DOCUMENTS 6,008,390 A 12/1999 Hattori et al.
6,060,613 A 5/2000 Hattori et al.

FOREIGN PATENT DOCUMENTS

EP 1 156 033 11/2001

OTHER PUBLICATIONS

W. Mei Wu, et al., Journal of Pharmaceutical Sciences, vol. 76, No. 7, XP–002233731, pp. 508–512, "Enhancement of the Rectal Absorption of Sodium Ampicillin by N–Acylamino Acids in Rats", Jul. 1987.
Patent Abstracts of Japan, JP 05–070418, Mar. 23, 1993.

Primary Examiner—Deborah D. Carr
(74) Attorney, Agent, or Firm—Oblon, Spivak, McClelland, Maier & Neustadt, P.C.

(57) ABSTRACT

A method for preparing a highly purified N-long chain acyl neutral amino acid for use of a detergent and the like in a simple and convenient manner and in a high yield by reacting a neutral amino acid such as glycine, γ-aminobutyric acid, and alanine, with a saturated or unsaturated fatty acid halide having 8 to 22 carbon atoms, wherein the reaction is performed in a mixture of water and one or more kinds of hydrophilic organic solvents selected from the group consisting of acetone, acetonitrile, a secondary alcohol having 3 or 4 carbon atoms, and a tertiary alcohol having 4 carbon atoms such as isopropanol, sec-butanol, and tert-butanol in the presence of a base.

6 Claims, 1 Drawing Sheet

METHOD FOR PREPARING N-LONG CHAIN ACYL NEUTRAL AMINO ACID

FIELD OF THE INVENTION

The present invention relates to a method for preparing a highly purified N-long chain acyl neutral amino acid, which is useful for manufacture of detergents and the like, in a simple and convenient manner and in a high yield.

RELATED ART

Amine salts or alkali metal salts of N-long chain acyl neutral amino acids have superior surface activating and bacteriostatic action and also have low irritancy. Accordingly, they are useful for manufacture of detergents with a mild action to the skin. Since these amine salts or alkali metal salts of N-long chain acyl neutral amino acids are often utilized as a detergent component of quasi drugs and cosmetics, they are required to have as little smell and impurities as possible. In particular, impurities may affect functions or feelings inherently achieved by the compounds. As a method for preparing the N-long chain acylamino acid, in general, a method is known which comprises the steps of condensing an amino acid and a fatty acid halide under an alkali condition by the Schotten-Baumann reaction, and then isolating the product as an acylamino acid by using an acid.

As for preparation of acyl neutral amino acids, it is known that the reaction advances even though water alone is used as a solvent, as disclosed in Japanese Patent Unexamined Publication (Kokai) Nos. 7-157795 and 5-70418. However, when water alone is used as a solvent, a purity of the acylated compound does not exceed a level of little more than about 90%, and it is difficult to obtain the compound with a high purity. Further, the reaction system suffers from extremely high viscosity of a reaction mixture, which results in insufficient stirring at a high concentration and a further deterioration of a purity. Therefore, the reaction is inevitably carried out at a low concentration that allows stirring, and for this reason, the reaction is economically disadvantageous. As an economical method performable at a high concentration, a method is disclosed in the aforementioned patent document which involves an increase of a reaction temperature with a progress of the acylation. However, also in this method, viscosity of the reaction mixture is still high to load equipments, and further, if uniform starring is insufficient, a deterioration of a purity may sometimes arise.

As a method for obtaining an acylamino acid with a high purity, the water/acetone mixed-solvent method is generally used for acidic amino acids. Although this system successfully gives a target substance with a high purity, no tendency of viscosity reduction due to the presence of the organic solvent is observed. Japanese Patent Publication (Kokoku) No. 51-38681 discloses a method of using a primary alcohol as a reaction solvent for condensation of an amino acid and a fatty acid halide in the presence of an alkali. However, in this reaction, low concentrations of the reaction species are applied to perform the reaction in a region where sufficient stirring is possible with water alone, and therefore, the aforementioned patent document neither suggests nor teaches a possibility of viscosity reduction by use of a primary alcohol. Further, although this method enables preparation of the target substance with high purity, an ester may possibly be produced by the reaction of the primary alcohol and fatty acid chloride and heating under an acidic condition after the reaction, which arises problems of degradation of properties such as foaming property and generation of smell of the produced ester.

As a method for purifying an N-long chain acyl neutral amino acid, a method is disclosed in Japanese Patent Unexamined Publication No. 5-70418 which comprises isolation of an N-long chain acylamino acid as crystals and washing said crystals. However, this method requires an apparatus for separating the crystals, and the step of washing with water needs undesirably prolonged period of time when certain kinds of acylamino acids have poor crystallizing properties. Accordingly, the method is not desirable from viewpoints of facilities and efficiency. Further, Japanese Patent Unexamined Publication No. 7-157795 discloses a method of desalting an N-long chain acylamino acid in water by adding a fatty acid or the like so as to facilitate separation of an organic layer and an aqueous layer. However, this method has a problem in that a purity of the N-long chain acylamino acid is degraded.

SUMMARY OF THE INVENTION

An object of the present invention is to provide a method for obtaining a highly purified N-long chain acyl neutral amino acid efficiently and in a high yield. Further, another object of the present invention is to provide a method for preparing an N-long chain acyl neutral amino acid, which enables easy isolation of a highly purified N-long chain acyl neutral amino acid in a simple and convenient manner.

The inventors of the present invention conducted various researches to achieve the aforementioned objects. As a result, they found that, for preparation of an N-long chain acyl neutral amino acid by a reaction of a neutral amino acid and a fatty acid halide, when a mixture of water and one or more kinds of hydrophilic organic solvents selected from the group consisting of acetone, acetonitrile, a secondary alcohol having 3 or 4 carbon atoms, and a tertiary alcohol having 4 carbon atoms is used as a solvent, viscosity of the reaction mixture was markedly reduced compared with a process where the reaction was performed by using water as a sole solvent, and thus the reaction yield was be remarkably improved. They further found that, when the resulting reaction mixture was heated under an acidic condition, rapid separation of an organic layer and an aqueous layer occurred, thereby desalting was more efficiently conductible than the system utilizing water as a sole solvent. The present invention was achieved on the basis of these findings.

The present invention thus provides a method for producing an N-long chain acyl neutral amino acid by a reaction of a neutral amino acid and a saturated or unsaturated fatty acid halide having 8 to 22 carbon atoms, wherein the reaction is performed in a mixture of water and one or more kinds of hydrophilic organic solvents selected from the group consisting of acetone, acetonitrile, a secondary alcohol having 3 or 4 carbon atoms, and a tertiary alcohol having 4 carbon atoms in the presence of a base.

According to preferred embodiments of the present invention, provided are the aforementioned method, wherein the hydrophilic organic solvent consists of one or more kinds of hydrophilic organic solvents selected from the group consisting of isopropanol, sec-butanol, and tert-butanol; the aforementioned method, wherein the hydrophilic solvent consists of tert-butanol; and the aforementioned method, wherein the neutral amino acid is glycine, γ-aminobutyric acid, alanine, valine, leucine, isoleucine, serine, or threonine.

The present invention further provides the aforementioned method, which further comprises the steps of warming a reaction mixture adjusted to pH 1 to 6 to a temperature of 35° C. or higher for separation of an organic layer and an aqueous layer, and recovering the N-long chain acyl neutral amino acid from the organic layer. More specifically, the present invention provides a method for preparing an N-long chain acyl neutral amino acid by a reaction of a neutral amino acid and a saturated or unsaturated fatty acid halide having 8 to 22 carbon atoms, which comprises the following steps of (1) performing the reaction in a mixture of water and one or more kinds of hydrophilic organic solvents selected from the group consisting of acetone, acetonitrile, a secondary alcohol having 3 or 4 carbon atoms, and a tertiary alcohol having 4 carbon atoms in the presence of a base, and (2) warming a reaction mixture adjusted to pH 1 to 6 to a temperature of 35° C. or higher for separation of an organic layer and an aqueous layer, and recovering the N-long chain acyl neutral amino acid from the organic layer.

According to the preparation method of the present invention, highly purified N-long chain acyl neutral amino acids, which are useful for manufacture of detergents and the like, can be prepared in a high yield in a simple and convenient manner.

PREFERRED EMBODIMENTS OF THE INVENTION

Figure 1:
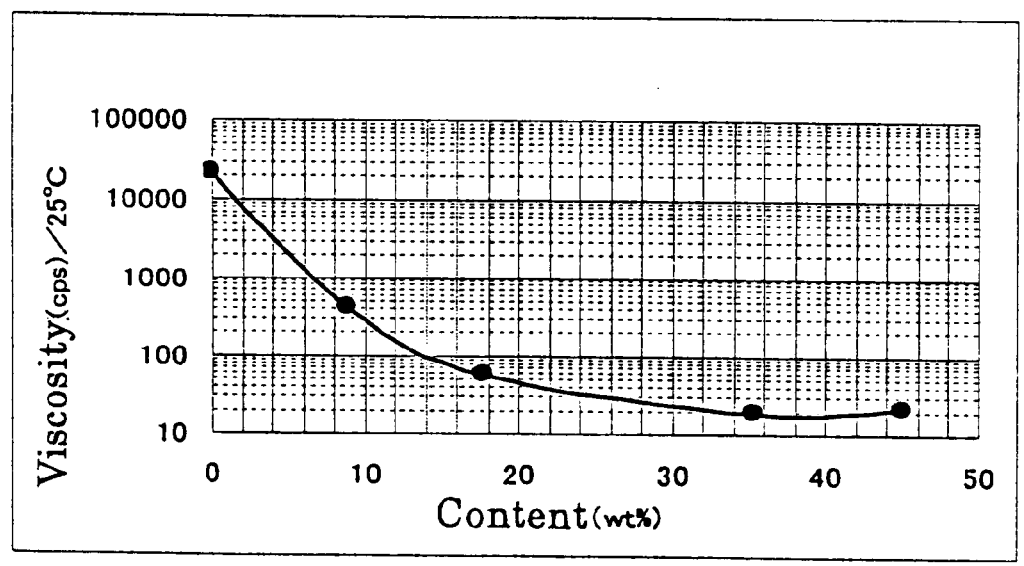
FIG. 1 shows results of viscosity measurement of reaction mixtures in which the amount of tert-butanol in a reaction solvent was changed.

The method of the present invention is characterized in that, for the preparation of an N-long chain acyl neutral amino acid by a reaction of a neutral amino acid and a fatty acid halide having 8 to 22 carbon atoms, the reaction is performed in a mixture of water and one or more kinds of hydrophilic organic solvents selected from the group consisting of acetone, acetonitrile, a secondary alcohol having 3 or 4 carbon atoms, and a tertiary alcohol having 4 carbon atoms in the presence of a base.

Types of the neutral amino acid are not particularly limited. Various amino acids including α-amino acids, β-amino acids and the like can be used, and amino acids in optically pure forms, any mixtures of optical isomers, racemates, diastereomers in a pure form or any mixtures thereof and the like can be used. More specifically, examples include glycine, alanine, valine, leucine, isoleucine, phenylalanine, methionine, proline, serine, threonine, β-alanine, γ-aminobutyric acid and the like. A mixture of two or more kinds of neutral amino acids can also be used as a raw material.

The fatty acid halide used in the present invention is a halide of a long chain fatty acid, more specifically, a saturated or unsaturated fatty acid halide having 8 to 22 carbon atoms. The carbon chain of the fatty acid halide may be straight, branched or cyclic, or a combination thereof, and the chain may contain one or more unsaturated bonds. A mixture of two or more kinds of fatty acid halides may also be used as a raw material. More specifically, examples of the fatty acid halide include fatty acid halides consisting of single kind of fatty acid halide such as caprylic acid halide, lauric acid halide, myristic acid halide, palmitic acid halide, stearic acid halide, and oleic acid halide, and fatty acid halides consisting of mixture of fatty acid halides such as coconut oil fatty acid halide and tallow fatty acid halide and the like.

As the hydrophilic organic solvent, one or more kinds of solvents selected from acetone, acetonitrile, a secondary alcohol having 3 or 4 carbon atoms, and a tertiary alcohol having 4 carbon atoms can be used. Alcohols, more specifically, isopropanol, sec-butanol, and tert-butanol are more preferred from a viewpoint of a temperature condition and the like for the separation of an organic layer and aqueous layer. Among them, tert-butanol is most preferred from a viewpoint of a foaming property of a final product, smell of the solvent and the like.

A content of the hydrophilic organic solvent in the reaction solvent is not particularly limited. The hydrophilic organic solvent concentration in the mixed solvent of hydrophilic organic solvent and water is preferably, for example, 5 to 60 wt % at the step of dissolution of the amino acid before the acylation. When the content is less than 5 wt %, a viscosity decreasing effect may sometimes become lowered, which results difficulty in the reaction at a high concentration. When the concentration exceeds 60 wt %, a reaction yield and a viscosity decreasing effect for the reaction mixture cannot be improved, which results in time consuming for removal of the solvent. From a viewpoint of easiness of removal of the organic solvent and the like, the concentration of the hydrophilic organic solvent in the reaction solvent may preferably be 5 to 50 wt %.

Types of the base used for the reaction are not particularly limited. For example, metal hydroxides such as sodium hydroxide or potassium hydroxide can be used. For the reaction of the neutral amino acid and the fatty acid halide, methods for introducing the reaction species into a reaction system are not particularly limited. For example, an example includes a method of mixing given amounts of neutral amino acid, a reaction solvent, and a whole amount of a base required for the reaction in a reaction tank, and then adding a fatty acid chloride into the mixture. For the above method, a pH of the reaction mixture after completion of the reaction is desirably 9 or higher. Alternatively, another example includes a method of mixing given amounts of neutral amino acid, a reaction solvent, and a part of a base in a reaction tank, and then adding a fatty acid chloride and a remaining amount of base while a pH is adjusted in the range of 9 to 14. In the two methods exemplified above, the reaction temperature is 0 to 60° C., preferably 5 to 50° C., more preferably 10 to 45° C.

Concentrations of the neutral amino acid and the fatty acid halide in the reaction mixture are not particularly limited, and may vary depending on a type of neutral amino acid, a type of fatty acid halide, and a type of base used for the reaction. Upon completion of the reaction, the concentration of the N-long chain acyl neutral amino acid, which is a reaction product, is desirably 18 wt % or more, preferably 20 wt % or more, from a economic point of view and the like. The concentration is more preferably 22 weight % or more. By the aforementioned reaction, a neutral amino acid and a fatty acid halide can be reacted both at high concentrations, and an N-long chain acyl neutral amino acid can be efficiently prepared in a high yield.

According to a preferred embodiment of the method of the present invention, after completion of the aforementioned reaction, a pH of the reaction mixture is adjusted to be in the range of 1 to 6, and then the reaction mixture is warmed to a temperature of 35° C. or higher for separation of an organic layer and an aqueous layer, and the N-long chain acyl neutral amino acid can be recovered from the organic layer. By employing the aforementioned method, desalting can be efficiently performed, and thus a highly purified target substance can be obtained in a higher yield.

A type of the acid used for adjusting the pH is not particularly limited. For example, mineral acids such as hydrochloric acid or sulfuric acid can be preferably used. After the adjustment of the pH, an organic layer and an aqueous layer can be separated by warming the reaction mixture to a temperature of 35° C. or higher. When the temperature of the reaction mixture is lower than 35° C., the separation may become time consuming or no separation of the layers may be achievable. Although an upper limit of the temperature of the reaction mixture is not particularly limited, a boiling point of water or the hydrophilic organic solvent, whichever is lower, may preferably be chosen as the upper limit of the temperature, because a pressurization apparatus or the like is required if the temperature exceeds a boiling point of a solvent. When a hydrophilic organic solvent having a relatively low boiling point such as acetone is used, the separation can be performed by warming to a temperature of about 70° C. under pressurization.

By the separation of an organic layer and an aqueous layer, salts in the reaction system can be removed into the aqueous layer, and the organic layer from which the salts are substantially removed can be recovered. In order to further improve the removal efficiency of the salts, a method may be employed which comprises the steps of mixing the organic layer obtained by the layer separation with water and/or the hydrophilic organic solvent, separating the mixture into an organic layer and an aqueous layer again at a temperature of 35° C. or higher to recover the organic layer.

After the organic layer obtained is dried and the solvent is removed, an alkaline substance can be added to the residue and dissolved to prepare an N-long chain acyl neutral amino acid as a surfactant. Alternatively, a surfactant can also be prepared by neutralizing the organic layer obtained by the layer separation with an alkaline substance to prepare an aqueous solution of the surfactant containing the organic solvent, and subjecting the resulting solution to concentration under reduced pressure or the like to remove the organic solvent. The alkaline substance used in the above process can be appropriately chosen from those generally used for preparation of surfactants. For example, examples include alkali metals such as sodium and potassium, alkaline earth metals such as calcium and magnesium, alkaline substances containing a metal such as aluminum or zinc, ammonia, organic amines such as monoethanolamine, diethanolamine and triethanolamine, basic amino acids such as arginine and lysine and the like.

EXAMPLES

The present invention will be more specifically explained with reference to the following examples. However, the present invention is not limited by the following examples.

Acylation purity mentioned in the examples can be calculated by using the following equation. Each weight in the equation was measured by high performance liquid chromatography (HPLC).

Acylation purity=(Weight of acyl neutral amino acid)/(Weight of acyl neutral amino acid+Weight of fatty acid)×100 (%)

Example 1
Preparation of N-coconut Oil Fatty Acid Acyl-glycine Salt 30.0 g of glycine was dissolved in 189 g of water, 41 g of isopropanol (content of hydrophilic organic solvent: 17.8 wt %) and 9.5 g of sodium hydroxide to prepare an aqueous solution at pH 10. This aqueous solution was added with 87.6 g of coconut oil fatty acid chloride over about 1 hour, while a pH was adjusted to 10 by using 27% NaOH. During this operation, the reaction temperature was maintained at 15 to 20° C. After the addition of the acid chloride, the reaction mixture was stirred at the same temperature for about 1 hour. About 23% of N-coconut oil fatty acid acyl-glycine was contained in 437 g of the resulting reaction mixture, and the acylation purity was 96%. The resulting reaction mixture was adjusted to pH 1.8 with addition of 30.3 g of 75% sulfuric acid and then heated to 70° C. After stirring for 15 minutes, the reaction mixture was left standing to allow the reaction mixture separated into an organic layer (171 g) and an aqueous layer (296 g) within several minutes. The resulting organic layer was neutralized to pH 8.3 with 48% potassium hydroxide to obtain an about 30% solution of N-coconut oil fatty acid acyl-glycine potassium salt (containing isopropanol), and then the isopropanol was evaporated by concentration under reduced pressure (about 140 mmHg). In this operation, the isopropanol was evaporated while 95 g of water was gradually added so as to maintain the concentration at about 30%. After the evaporation, the concentration of the product was adjusted to 30% to obtain 375 g of N-coconut oil fatty acid acyl-glycine potassium salt solution.

Examples 2 and 3
Preparation of N-coconut Oil Fatty Acid Acyl-glycine Salt

A reaction was performed in the same manner as in Example 1, except that tert-butanol (Example 2) or acetone (Example 3) was used instead of isopropanol. For each of the solvents, the reaction mixture obtained was found to contain about 23% of N-coconut oil fatty acid acyl-glycine. Acylation purities were 97% and 96%, respectively.

Comparative Example 1
Preparation of N-coconut Oil Fatty Acid Acyl-glycine Salt 30.0 g of glycine was dissolved in 230 g of water and 9.5 g of sodium hydroxide to prepare an aqueous solution at pH 10. The resulting aqueous solution was added with 87.6 g of coconut oil fatty acid chloride over about 1 hour, while a pH was adjusted to 10 by using 27% NaOH. During this operation, the reaction temperature was gradually increased from 25° C. with addition of the acid chloride. At the end of the addition of the acid chloride, the reaction temperature was 50° C. Then, the reaction mixture was stirred at the same temperature for about 1 hour. About 22% of N-coconut oil fatty acid acyl-glycine was contained in the resulting reaction mixture, and the acylation purity was 92%. The reaction mixture obtained was adjusted to pH 1.8 with addition of 31 g of 75% sulfuric acid and heated to 75° C. After stirring for 15 minutes, the reaction mixture was left standing for 30 minutes. As a result, the organic layer was in an emulsified state, and the layer separation state was extremely poor. Thus, the following processes was not performable.

Comparative Example 2

The same reaction as Comparative Example 1 was performed, and then 435 g of the resulting reaction mixture was added with 130 g of water. After the addition, the concentration of the N-coconut oil fatty acid acyl-glycine was about 17%. This reaction mixture was added with 31 g of 75% sulfuric acid, heated to 75° C., stirred for 15 minutes, and then left standing for 30 minutes. Although the organic layer was in an emulsified state, 139 g of aqueous layer portion was removable. The residue was added with 139 g of water, heated at 80° C. and then stirred for 15 minutes. After being left standing for 15 minutes, the organic layer was separated as an oil. 371 g of aqueous layer was removed, and 225 g of the resulting organic layer was neutralized to pH 8.3 with 48% potassium hydroxide. Then, the concentration of the product was adjusted to 30% to obtain 345 g of a solution of N-coconut oil fatty acid acyl-glycine potassium salt.

Viscosities of the reaction mixtures, acylation purities, separation temperatures, solid contents in the organic layer portions after the separation, and chlorine contents in the N-coconut oil fatty acid acyl-glycine potassium salt solutions as the final products are shown in Table 1 for Examples 1, 2, 3 and Comparative Example 2. From the results shown in Table 1, it can be understood that use of water alone results in an extremely high viscosity of the reaction mixture and results in a low desalting efficiency proved by the poor layer separability in the separation of the organic layer and aqueous layer and the low solid content in the organic layer after the separation. For example, when the upper layer obtained after the first layer separation in Comparative Example 2 was made into a 30% N-coconut oil fatty acid acyl-glycine potassium salt solution by using 48% sodium hydroxide, the solution gave a Cl content of 3%.

TABLE 1

| Solvent | Example 1 Water/IPA | Example 2 Water/t-BuOH | Example 3 Water/acetone | Comparative Example 2 Water |
|---|---|---|---|---|
| Viscosity of reaction mixture (cps/25° C.) | 31 | 57 | 24 | 21000 |
| Acylation purity (wt %) | 97 | 97 | 96 | 92 |
| Separation temperature under acidic condition (° C.) | 70 | 70 | 70 (under pressurization) | 75–80 |
| Solid content in organic layer (wt %) | 64.5 | 65.2 | 67.7 | 32.5 (after second separation) |
| Cl content in product (%) | 0.27 | 0.25 | 0.20 | 0.80 (after second separation) |

Examples 4, 5, and 6

In the reaction of Examples 2, viscosity of the reaction mixture was measured with a change of a content of tert-butanol in the reaction solvent. The results are shown in FIG. 1. The reaction conditions were the same as those applied in Example 2. It can be understood that a sufficient decrease of viscosity of the reaction mixture was attained by using tert-butanol as the hydrophilic organic solvent. In Example 4, tert-butanol concentration was 8.9% (tert-butanol (20.5 g)/water (209.5 g)), in Example 5, tert-butanol concentration was 35.4% (tert-butanol (81.5 g)/water (148.5 g)), and in Example 6, tert-butanol concentration was 45.0% (tert-butanol (103.5 g)/water (126.5 g)).

Example 7
Preparation of N-lauroylglycine Salt 30.0 g of glycine was dissolved in 148.5 g of water, 81.5 g of isopropyl alcohol (content of hydrophilic organic solvent: 35.5 wt %) and 9.5 g of sodium hydroxide to prepare an aqueous solution at pH 10. The resulting aqueous solution was added with 84.9 g of lauroyl chloride over about 1 hour, while a pH was adjusted to 10 by using 27% NaOH. During this operation, the reaction temperature was maintained at 15 to 20° C. After the addition of the acid chloride, the reaction mixture was stirred at the same temperature for about 1 hour. About 22% of N-lauroylglycine was contained in 433 g of the reaction mixture obtained, and the acylation purity was 97%. Viscosity of the reaction mixture was 15 cps at 25° C. The resulting reaction mixture was adjusted to pH 1.8 with addition of 30.0 g of 75% sulfuric acid and heated to 65° C. After stirring for 15 minutes, the reaction mixture was left standing to allow the reaction mixture separated into an organic layer (200 g) and an aqueous layer (263 g) within several minutes. The organic layer was neutralized to pH 8.3 with 48% potassium hydroxide to obtain an about 30% solution of N-lauroylglycine potassium salt (containing isopropanol), and then isopropanol was evaporated by concentration under reduced pressure in the same manner as in Example 1. After the evaporation, the concentration of the salt was adjusted to 30% to obtain 370 g of N-lauroylglycine potassium salt solution.

Example 8
Production of N-lauroylglycine Salt

The procedure of Example 7 was repeated except that t-butanol was used instead of isopropanol. About 22% of N-lauroylglycine was contained in the reaction mixture obtained, and the acylation purity was 98%. Viscosity of the reaction mixture was 19 cps at 25° C. By this reaction, 370 g of N-lauroylglycine potassium salt solution was obtained.

Comparative Example 3
Production of N-lauroylglycine Salt

The procedure of Example 7 was repeated except that ethanol was used instead of isopropanol. Deposition of lauroylglycine salt was observed in the reaction mixture at the addition of the acid chloride, and the reaction mixture was in a state of slurry after completion of the reaction. About 22% of N-lauroylglycine was contained in the reaction mixture obtained, and the acylation purity was 95%. By this reaction, 365 g of N-lauroylglycine potassium salt solution was obtained.

Test Example 1

The N-lauroylglycine potassium salt solutions obtained in Examples 7, 8, and Comparative Example 3 were evaluated in hand washing test performed by a panel of five experts. The results are shown in Table 2.

TABLE 2

| | Comparative Example 3 | Example 7 | Example 8 |
|---|---|---|---|
| Smell of test solution | Ethyl laurate-like smell | Substantially no smell | Substantially no smell |
| Volume of foam | Standard | Comparative to standard | Slightly more foamy |
| Quality of foam | Standard | Comparative to standard | Comparative to standard |
| Smell during washing | Ethyl laurate-like smell | Substantially no smell | Substantially no smell |
| Feeling during rinsing | Standard | Comparative to standard | Slightly less sliminess |

Example 9
Preparation of N-cocoyl-L-alanine Salt 35.6 g of L-alanine was dissolved in 163.5 g of water, 35.4 g of tert-butanol (content of organic solvent: 17.8 wt %) and 8.1 g of sodium hydroxide to prepare an aqueous solution at pH 10. Then, the resulting aqueous solution was added with 87.7 g of cocoyl chloride over about 1 hour, while a pH was adjusted to 10 by using 27% NaOH. During this operation, the reaction temperature was maintained at 15–20° C. After the addition of the acid chloride, the reaction mixture was stirred at the same temperature for about 1 hour. About 26% of N-cocoyl-L-alanine was contained in 415 g of the reaction mixture obtained, and the acylation purity was 97%. Viscosity of this reaction mixture was 97 cps at 25° C. Further, the resulting reaction mixture was adjusted to pH 1.8 with addition of 29.1 g of 75% sulfuric acid and heated to 70° C. After stirring for 15 minutes, the reaction mixture was left standing to allow the reaction mixture separated into an organic layer (150 g) and an aqueous layer (292 g) within several minutes. The organic layer was neutralized to pH 7.0 with 90% aqueous triethanolamine to obtain an about 30% solution of N-cocoyl-L-alanine triethanolamine salt (containing tert-butanol), and then the tert-butanol was evaporated by concentration under reduced pressure in the same manner as in Example 1 (200 g of water was added). After the evaporation, the concentration of the salt was adjusted to 30% to obtain 520 g of N-cocoyl-L-alanine potassium salt solution. This aqueous solution had a Cl content of 0.05%.

Comparative Example 4
Preparation of N-cocoyl-L-alanine Salt 35.6 g of L-alanine was dissolved in 198.9 g of water and 8.1 g of sodium hydroxide to prepare an aqueous solution at pH 10. Then, the aqueous solution was added with 87.7 g of cocoyl chloride over about 1 hour, while a pH was adjusted to 10 by using 27% NaOH. During this operation, the reaction temperature was gradually increased from 25° C. with addition of the acid chloride. At the end of the addition of the acid chloride, the reaction temperature was 45° C. Then, the reaction mixture was stirred at the same temperature for about 1 hour. As a result of analysis of the reaction mixture obtained, the acylation purity was found to be 85%. Further, viscosity of this reaction mixture was 4000 cps at 25° C. The resulting reaction mixture was added with 120 g of water in view of handling property, and then subjected to layer separation process. The organic layer obtained was subjected to layer separation process again by using water in the same amount as that of the extracted water. The resulting organic layer was neutralized to pH 7.0 with 98% triethanolamine, and the concentration of the salt was adjusted to 30% to obtain a solution of N-cocoyl-L-alanine triethanolamine salt.

Example 10
Preparation of N-cocoyl-DL-alanine Salt

A reaction was performed in the same manner as in Example 9 except that DL-alanine and acetone were used instead of L-alanine and tert-butanol, respectively. The acylation purity in the reaction mixture obtained was 96.5%. Further, the resulting reaction mixture was separated into an organic layer and an aqueous layer at 75° C., and a solution of N-cocoyl-DL-alanine triethanolamine salt was obtained in the same manner as in Example 9. This aqueous solution had a Cl content of 0.08%.

Example 11
Preparation of N-myristoyl-L-alanine Salt 35.6 g of L-alanine was dissolved in 187.7 g of water, 42.3 g of tert-butanol (content of organic solvent: 18.4 wt %) and 6.8 g of sodium hydroxide to prepare an aqueous solution at pH 10. Then, this aqueous solution was added with 98.7 g of myristoyl chloride over about 1 hour, while a pH was adjusted to 10 by using 27% NaOH. During this operation, the reaction temperature was maintained at 25° C. After the addition of the acid chloride, the reaction mixture was stirred at the same temperature for about 1 hour. About 26% of N-myristoyl-L-alanine was contained in 461 g of the reaction mixture obtained, and the acylation purity was 97.6%. Further, the resulting reaction mixture was adjusted to pH 1.7 with addition of 29.4 g of 75% sulfuric acid and heated to 60° C. After stirring for 15 minutes, the reaction mixture was left standing, and the reaction mixture separated into an organic layer (176 g) and an aqueous layer (313 g) within several minutes. The resulting organic layer was further added with 250 g of 10 wt % aqueous tert-butanol, stirred and left standing for separation in the same manner. The resulting organic layer was neutralized to pH 7.0 with 90% aqueous triethanolamine to obtain an about 30% solution of N-myristoyl-L-alanine triethanolamine salt (containing tert-butanol), and then the tert-butanol was evaporated by vacuum concentration in the same manner as in Example 1 (400 g of water was added). The concentration of the salt was adjusted to 30% to obtain 585 g of N-myristoyl-L-alanine triethanolamine salt solution. This aqueous solution had a Cl content of less than 0.05%.

Example 12
Preparation of N-lauroyl-L-threonine Salt 49.0 g of L-threonine was dissolved in 214.5 g of water, 61.0 g of tert-butanol (content of organic solvent: 22.1 wt %) and 15.7 g of sodium hydroxide to prepare an aqueous solution at pH 11. Then, this aqueous solution was added with 87.4 g of lauroyl chloride over about 1 hour, while a pH was adjusted to 11 by using 27% NaOH. During this operation, the reaction temperature was maintained at 20–30° C. After the addition of the acid chloride, the reaction mixture was stirred at the same temperature for about 1 hour. About 24% of N-lauroyl-L-threonine was contained in 490 g of the reaction mixture obtained, and the acylation purity was 96.5%. The resulting reaction mixture was added with 29.0 g of 75% sulfuric acid and heated to 55° C. After stirring for 15 minutes, the reaction mixture was left standing to allow the reaction mixture separated into an organic layer (190 g) and an aqueous layer (329 g) within several minutes. The resulting organic layer was further added with 300 g of 10 wt % aqueous tert-butanol, stirred and left standing for separation in the same manner. This operation was repeated twice. The resulting organic layer was neutralized to pH 8.0 with 48% potassium hydroxide to obtain an about 25% solution of N-lauroyl-L-threonine potassium salt (containing tert-butanol), and then the tert-butanol was evaporated by concentration under reduced pressure in the same manner as in Example 1 (320 g of water was added). After the evaporation, the concentration of the salt was adjusted to 25% to obtain 530 g of N-lauroyl-L-threonine potassium salt solution. This aqueous solution had a Cl content of less than 0.05%.

Example 13
Preparation of N-lauroyl-γ-aminobutyric Acid Salt 42.5 g of γ-aminobutyric acid was dissolved in 166.0 g of water, 76.0 g of isopropyl alcohol (content of hydrophilic organic solvent: 31.4 wt %) and 12.7 g of sodium hydroxide to prepare an aqueous solution at pH 11. Then, the resulting aqueous solution was added with 87.4 g of lauroyl chloride over about 1 hour, while a pH was adjusted to 11 by using 27% NaOH. During this operation, the reaction temperature was maintained at 15° C. After the addition of the acid chloride, the reaction mixture was stirred at the same temperature for about 1 hour. About 25% of N-lauroyl-γ-aminobutyric acid was contained in 455 g of the reaction mixture obtained, and the acylation purity was 96.5%. The resulting reaction mixture was added with 32.0 g of 75% sulfuric acid and heated to 60° C. After stirring for 15 minutes, the reaction mixture was left standing to allow the reaction mixture separated into an organic layer (200 g) and an aqueous layer (287 g) within several minutes. The resulting organic layer was further added with 250 g of water, stirred at 70° C. and left standing for separation in the same manner. The resulting organic layer was neutralized to pH 8.0 with 48% potassium hydroxide to obtain an about 20% solution of N-lauroyl-γ-aminobutyric acid potassium salt (containing IPA). Then, the solution was concentrated to a concentration of 25% by evaporating water and isopropyl alcohol by vacuum concentration to obtain 500 g of N-lauroyl-γ-aminobutyric acid potassium salt solution. This aqueous solution had a Cl content of less than 0.05%.

Example 14

Preparation of N-cocoylglycine Salt 30.0 g of glycine was dissolved in 83.6 g of water, 48.4 g of tert-butanol (content of hydrophilic organic solvent: 34.2 wt %) and 6.8 g of sodium hydroxide to prepare an aqueous solution at pH 10. Then, the resulting aqueous solution was added with 87.7 g of cocoyl chloride over about 1 hour, while a pH was adjusted to 10 by using 27% NaOH. During this operation, the reaction temperature was maintained at 20–25° C. After the addition of the acid chloride, the reaction mixture was stirred at the same temperature for about 1 hour. About 30% of N-cocoylglycine was contained in 341 g of the reaction mixture obtained, and the acylation purity was 97%. Further, the resulting reaction mixture was adjusted to pH 1.8 with addition of 28.8 g of 75% sulfuric acid and heated to 70° C. After stirring for 15 minutes, the reaction mixture was left standing to allow the reaction mixture separated into an organic layer (160 g) and an aqueous layer (208 g) within several minutes. This organic layer was neutralized to pH 8.3 with 48% aqueous potassium hydroxide to obtain an about 30% solution of N-cocoylglycine potassium salt (containing tert-butanol), and then the tert-butanol was evaporated by concentration under reduced pressure in the same manner as in Example 1 (150 g of water was added). After the evaporation, the concentration of the salt was adjusted to 30% to obtain 370 g of N-cocoylglycine potassium salt solution. This aqueous solution had a Cl content of 0.14%.

Example 15

Sensory Evaluation

Formulations each containing the components shown in Table 3 were prepared by using the N-cocoyl-L-alanine triethanolamine salt solutions obtained in Example 9 and Comparative Example 4, and sensory evaluation was performed for finished feeling of a hairpiece after washing with the formulations.

TABLE 3

|  | Formulation Example 1 | Formulation Example 2 | Formulation Example 3 |
|---|---|---|---|
| N-Cocoyl-L-alanine triethanolamine salt solution obtained in Example 9 (purity: 97%) | 50 | — | 43 |
| N-Cocoyl-L-alanine triethanolamine salt solution obtained in Comparative Example 4 (purity: 85%) | — | 50 | — |
| Coconut oil fatty acid triethanolamine salt | — | — | 2 |
| Cationic cellulose | 0.2 | 0.2 | 0.2 |
| Water | Balance | Balance | Balance |

As a result of the sensory evaluation, it was found that Formulation Example 1 gave "dry" feeling, whereas Formulation Examples 2 and 3 gave "feathering and voluminous" feeling. Therefore, by using highly purified acylamino acids, formulations giving different feelings can easily be obtained.

Example 16

Hair Shampoo

Hair shampoo having the composition shown in Table 4 was prepared by using the product obtained in Example 10. This shampoo was found to have good foaming property, no creakiness during rinsing and dry feeling of hair after dryness.

TABLE 4

| | |
|---|---|
| 30% N-Cocoyl-DL-alanine triethanolamine salt solution obtained in Example 10 | 30 |
| 30% Coconut oil fatty acid amide propyldimethylaminoacetic acid betaine solution | 15 |
| Lauric acid diethanolamide | 3 |
| 1,3-Butylene glycol | 3 |
| Polyoxyethylene stearic acid ester | 0.5 |
| Trimethylglycine | 0.5 |
| Cationic cellulose | 0.2 |
| Citric acid | Appropriate amount |
| Antiseptic | Appropriate amount |
| Purified water | Balance |
| Total | 100 |
| PH 6.3 | |

What is claimed is:

1. A method for preparing an N-long chain acyl neutral amino acid by a reaction of a neutral amino acid and a saturated or unsaturated fatty acid halide having 8 to 22 carbon atoms, wherein the reaction is performed in a mixture of water and one or more kinds of hydrophilic organic solvents selected from the group consisting of acetone, acetonitrile, a secondary alcohol having 3 or 4 carbon atoms, and a tertiary alcohol having 4 carbon atoms in the presence of a base.

2. The method according to claim 1, wherein the hydrophilic organic solvent is at least one kind of hydrophilic organic solvent selected from the group consisting of isopropanol, sec-butanol, and tert-butanol.

3. The method according to claim 1, wherein the hydrophilic solvent is tert-butanol.

4. The method according to claim 1, wherein the neutral amino acid is glycine, γ-aminobutyric acid, alanine, valine, leucine, isoleucine, serine, or threonine.

5. The method according to any one of claims 1 to 4, which further includes the steps of warming a reaction mixture which is adjusted to a pH of 1 to 6 to a temperature of 35° C. or higher for separation of an organic layer and an aqueous layer, and then recovering the N-long chain acyl neutral amino acid from the organic layer.

6. A liquid or solid detergent composition, which is formulated by using an N-long chain acyl neutral amino acid prepared by the method according to any one of claims 1 to 5 or a salt thereof.

* * * * *